US00PP22021P2

(12) United States Plant Patent
Heuger

(10) Patent No.: US PP22,021 P2
(45) Date of Patent: Jul. 5, 2011

(54) ***HELLEBORUS* PLANT NAMED 'COSEH 720'**

(50) Latin Name: *Helleborus×ballardiae*
Varietal Denomination: COSEH 720

(76) Inventor: Josef Heuger, Glandorf (DE)

( * ) Notice: Subject to any disclaimer, the term of this patent is extended or adjusted under 35 U.S.C. 154(b) by 0 days.

(21) Appl. No.: 12/798,347

(22) Filed: Mar. 31, 2010

(51) Int. Cl.
*A01H 5/00* (2006.01)

(52) U.S. Cl. ..... Plt./439
(58) Field of Classification Search ..... Plt./439
See application file for complete search history.

*Primary Examiner* — Annette H Para
(74) *Attorney, Agent, or Firm* — C. A. Whealy

(57) ABSTRACT

A new and distinct cultivar of *Helleborus* plant named 'COSEH 720', characterized by its upright plant habit; uniform flowering habit; dark green-colored leaves with distinct venation; long flowering period; numerous single light green-colored flowers; and good garden performance.

2 Drawing Sheets

Botanical designation: *Helleborus×ballardiae.*
Cultivar denomination: 'COSEH 720'.

BACKGROUND OF THE INVENTION

The present invention relates to a new and distinct cultivar of *Helleborus* plant, botanically known as *Helleborus×ballardiae*, and hereinafter referred to by the name 'COSEH 720'.

The new *Helleborus* plant is a product of a planned breeding program in Glandorf, Germany. The objective of the breeding program was to create new uniform *Helleborus* cultivars with unique and attractive flower coloration and resistance to pests.

The new *Helleborus* plant originated from a cross-pollination conducted by the Inventor in Glandorf, Germany in November, 2002 of two unnamed proprietary seedling selections of *Helleborus×ballardiae*, not patented. The new *Helleborus* plant was discovered and selected by the Inventor as a single flowering plant from within the progeny of the stated cross-pollination grown in a controlled greenhouse environment in Glandorf, Germany in February, 2005.

Asexual reproduction of the new *Helleborus* plant by divisions in a controlled greenhouse environment in Glandorf, Germany since March, 2005, has shown that the unique features of this new *Helleborus* plant are stable and reproduced true to type in successive generations.

SUMMARY OF THE INVENTION

Plants of the new *Helleborus* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'COSEH 720'. These characteristics in combination distinguish 'COSEH 720' as a new and distinct cultivar of *Helleborus* plant:

1. Upright plant habit.
2. Uniform flowering habit.
3. Dark green-colored leaves with distinct venation.
4. Long flowering period.

5. Numerous single light green-colored flowers.
6. Good garden performance.

Compared to plants of the parent selections, plants of the new *Helleborus* flower more freely and more uniformly.

Plants of the new *Helleborus* can be compared to plants of *Helleborus niger×Helleborus lividus* 'COSEH 710', disclosed in U.S. Plant Pat. No. 21,063. Plants of the new *Helleborus* differ primarily from plants of 'COSEH 710' in the following characteristics:

1. Plants of the new *Helleborus* are more compact than and not as vigorous as plants of 'COSEH 710'.
2. Plants of the new *Helleborus* and 'COSEH 710' differ in leaf color.
3. Flowers of plants of the new *Helleborus* are light green in color whereas flowers of plants of 'COSEH 710' are light green in color with reddish pink overtones.

BRIEF DESCRIPTION OF THE PHOTOGRAPHS

The accompanying colored photographs illustrate the overall appearance of the new *Helleborus* plant, showing the colors as true as it is reasonably possible to obtain in colored reproductions of this type. Colors in the photographs may differ slightly from the color values cited in the detailed botanical description which accurately describe the colors of the new *Helleborus* plant.

The photograph on the first sheet comprises a side perspective view of a typical flowering plant of 'COSEH 720' grown in a container.

The photograph on the second sheet is a close-up view of a typical flower of 'COSEH 720'.

DETAILED BOTANICAL DESCRIPTION

The aforementioned photographs and following observations, measurements and values describe plants grown in Glandorf, Germany in 1.5-liter containers during the winter in a glass-covered greenhouse and under conditions which closely approximate commercial *Helleborus* production. During the production of the plants, day temperatures ranged from 12° C. to 32° C. and night temperatures ranged from 3° C. to 18° C. Plants were one year old when the photographs and the description were taken. In the following description, color references are made to The Royal Horticultural Society Colour Chart, 2007 Edition, except where general terms of ordinary dictionary significance are used.

Botanical classification: *Helleborus×ballardiae* 'COSEH 720'.

Parentage:

*Female, or seed, parent.*—Unnamed proprietary seedling selection of *Helleborus×ballardiae*, not patented.

*Male, or pollen, parent.*—Unnamed proprietary seedling selection of *Helleborus×ballardiae*, not patented.

Propagation:

*Type.*—By tissue culture.

*Time to initiate roots.*—About two months at 12° C.

*Time to produce a rooted young plant.*—About six months at 4° C. to 15° C.

*Root description.*—Thick to thin, fleshy; white to brown in color.

*Rooting habit.*—Sparse.

Plant description:

*Plant form and growth habit.*—Herbaceous perennial; upright plant habit with flowers held above the foliar plane; shape, globular; moderately vigorous growth habit.

*Plant height.*—About 29.9 cm.

*Plant diameter* (*area of spread*).—About 32.2 cm.

Foliage description:

*Arrangement.*—Leaves arranged in a basal rosette; palmately compound with five leaflets per leaf.

*Leaf length.*—About 13.1 cm.

*Leaf width.*—About 14.9 cm.

*Leaflet length.*—About 7.6 cm.

*Leaflet width.*—About 5.2 cm.

*Leaf shape.*—Palmate; orbicular in outline.

*Leaflet shape.*—Broadly ovate to broadly elliptic.

*Leaflet apex.*—Broadly acute.

*Leaflet base.*—Attenuate.

*Leaflet margin.*—Serrate.

*Leaflet texture, upper and lower surfaces.*—Smooth, glabrous; leathery.

*Leaflet venation pattern.*—Pinnate.

*Leaflet color.*—Developing leaves, upper surface: Between 137A to 137B and 143A. Developing leaves, lower surface: Close to N199A. Fully developed leaves, upper surface: Between 147A and N189A; venation, close to 144C. Fully developed leaves, lower surface: Between 148A and 191A; venation, between 178A to 178B and 183C to 183D. Petiole: Length: About 13 cm. Diameter: About 6 mm. Texture, upper and lower surfaces: Smooth, glabrous. Color, upper and lower surfaces: Close to 148B with spots, close to 177A to 177B.

Flower description:

*Flower shape and habit.*—Single rotate flowers; uniform flowering habit; about four flowers per terminal cyme; flowers facing outwardly to slightly nodding.

*Fragrance.*—None detected.

*Natural flowering season.*—Long flowering period; plants flower from late winter to early spring in Germany.

*Flower longevity on the plant.*—About ten days; flowers not persistent.

*Flower buds.*—Length: About 1.9 cm. Diameter: About 1.4 cm. Shape: Ovate. Color: Close to 145D.

*Inflorescence height.*—About 17.1 cm.

*Inflorescence diameter.*—About 11.7 cm.

*Flower diameter.*—About 6.2 cm.

*Flower depth* (*height*).—About 2 cm.

*Petals.*—Transformed into nectaries.

*Sepals.*—Arrangement: About five in a single whorl. Length: About 3 cm. Width: About 2.5 cm. Shape: Broadly ovate to broadly elliptic. Apex: Broadly acute. Margin: Entire. Texture, upper and lower surfaces: Smooth, glabrous. Color: When opening, upper surface: Close to 145C; towards the base, close to 145A to 145B. When opening, lower surface: Close to 145C to 145D; towards the base, close to 145B. Fully opened, upper surface: Close to 145D; towards the base, close to 145B to 145C; with development, color becomes closer to 145A. Fully opened, lower surface: Close to 145C to 145D; towards the base, close to 145C.

*Peduncles.*—Strength: Moderately strong. Length: About 12.8 cm. Diameter: About 6 mm. Aspect: About 15° from vertical. Texture: Smooth, glabrous. Color: Lighter than 151D with spots, close to 186D.

*Pedicels.*—Strength: Moderately strong. Length: About 1.3 cm. Diameter: About 2.5 mm. Aspect: About 30° from the peduncle axis. Texture: Smooth, glabrous. Color: Close to 145A.

*Reproductive organs.*—Stamens: Quantity per flower: About 90. Filament length: About 1 cm. Filament color: Close to 157D. Anther shape: Narrowly reniform. Anther length: About 2 mm. Anther color: Close to 1B to 1C. Pollen amount: Scarce. Pollen color: Close to 158D. Pistils: Quantity per flower: About six. Pistil length: About 9 mm. Stigma shape: Club-shaped. Stigma color: Close to 157D. Style length: About 8.5 mm. Style color: Close to 145D. Ovary color: Close to 145C to 145D. Nectaries (transformed petals): Quantity per flower: About eleven. Length: About 8 mm. Diameter, apex: Close to 3 mm. Diameter, base: Close to 1 mm. Shape: Flattened triangular. Color: Close to 144A; towards the apex, close to 144B.

*Seeds/fruits.*—Seed and fruit development have not been observed.

Garden performance: Plants of the new *Helleborus* have been observed to have good garden performance and to tolerate rain, wind and temperatures ranging from about −10° C. to about 35° C.

Pathogen/pest resistance: Plants of the new *Helleborus* have not been shown to be resistant to pathogens and pests common to *Helleborus*.

It is claimed:

1. A new and distinct *Helleborus* plant named 'COSEH 720' as illustrated and described.

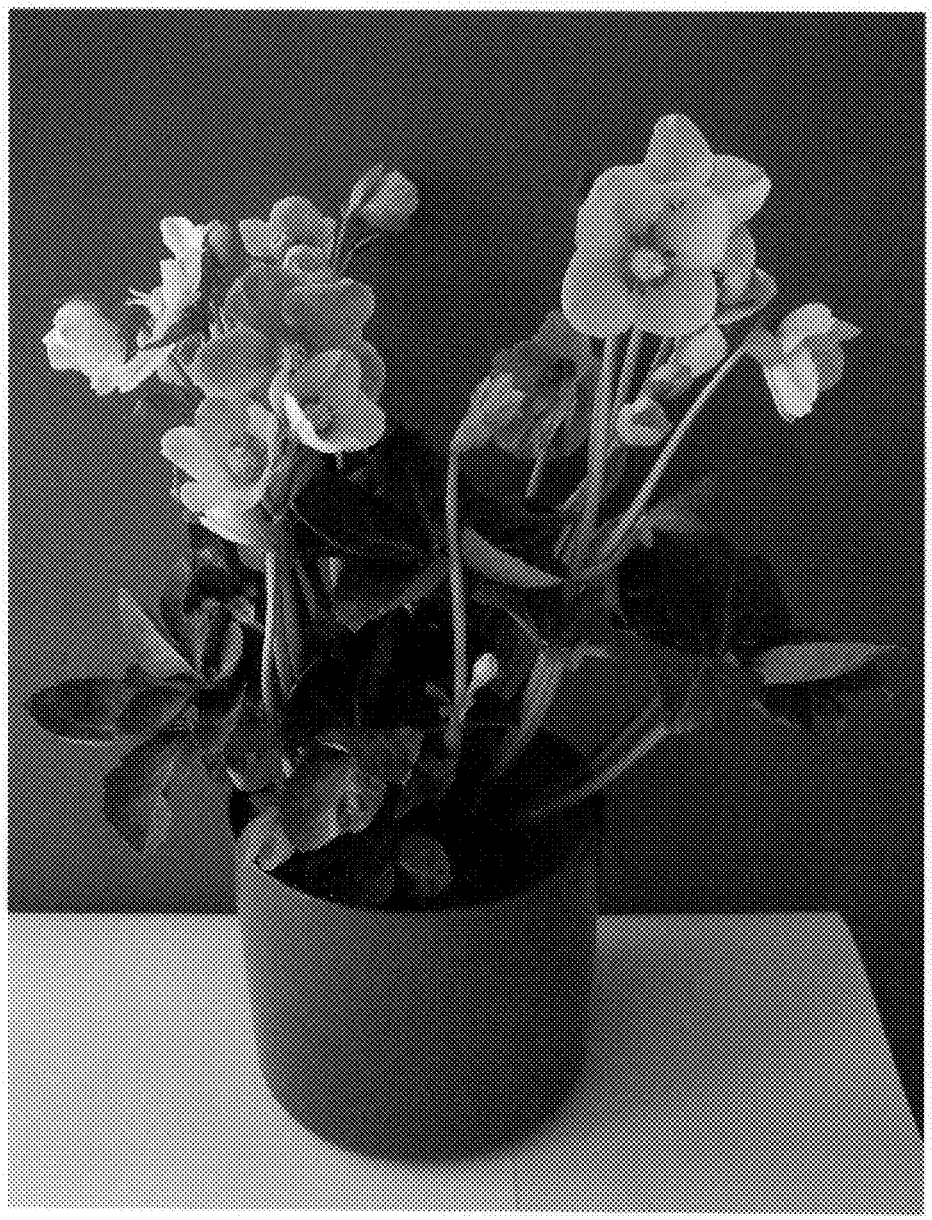

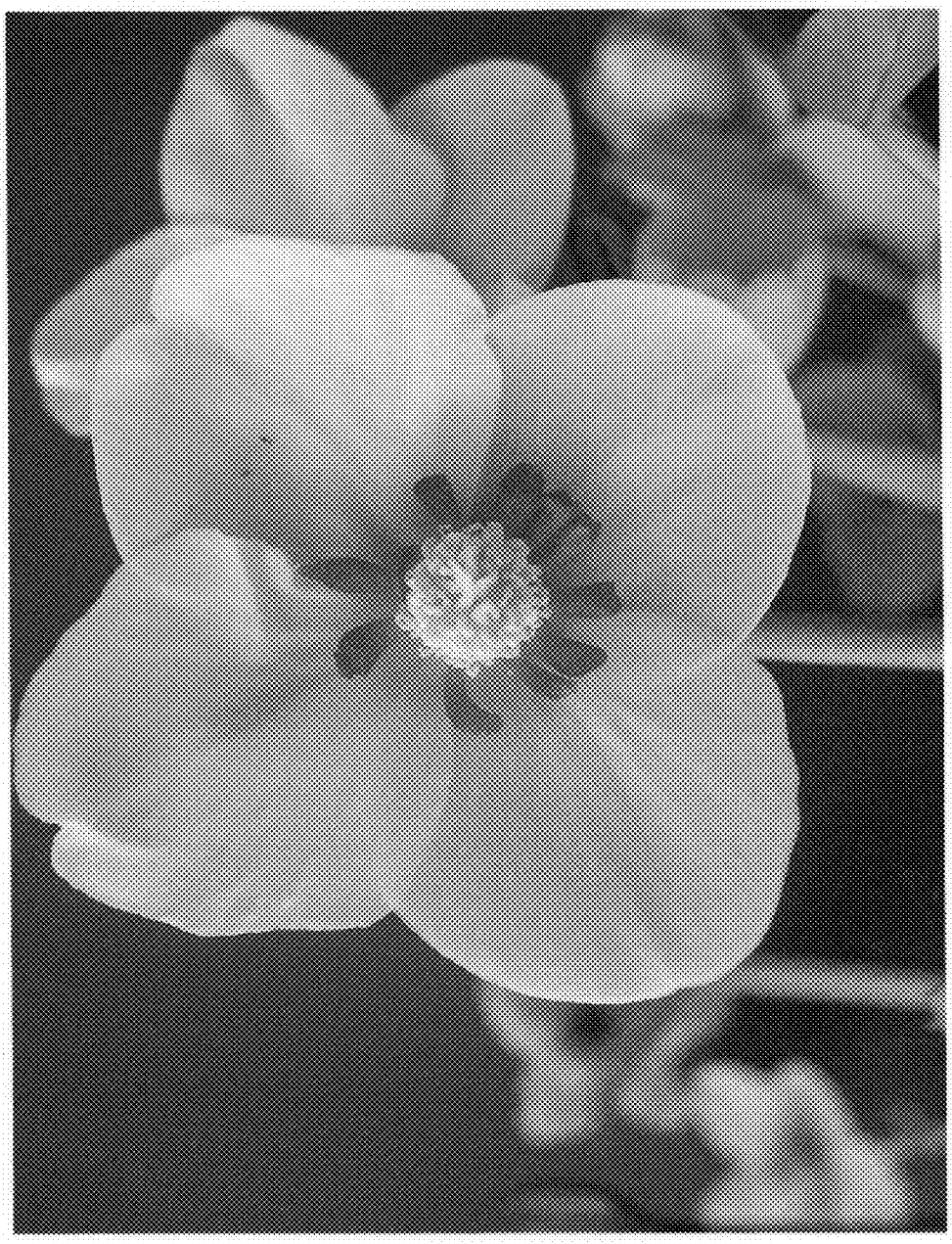

* * * * *